United States Patent [19]

Royon

[11] Plant 4,017

[45] Feb. 22, 1977

[54] ROSE PLANT-PITICA VARIETY

[75] Inventor: René Royon, Mougins, France

[73] Assignee: Universal Plants S. A. R. L., France

[21] Appl. No.: 633,952

[22] Filed: Nov. 20, 1975

[30] Foreign Application Priority Data

Dec. 4, 1974 Morocco ..... 16979

[51] Int. Cl.[2] ..... A01H 5/00

[52] U.S. Cl. ..... Plt./18

[58] Field of Search ..... Plt./18

*Primary Examiner*—Robert E. Bagwill

*Attorney, Agent, or Firm*—Burns, Doane, Swecker & Mathis

[57] ABSTRACT

A rose plant of the Grandiflora Class, obtained as a bud mutation of the variety Sweet Promise (known in the United States as Sonia) (U.S. Plant Pat. No. 3,095).

16 Drawing Figures

SUMMARY OF THE INVENTION

The object of the present invention is a variety of rose plant, of the Grandiflora Class, whose vegetative type corresponds to that of the variety Sweet Promise (known in the United States as Sonia) (U.S. Plant Pat. No. 3,095), but whose flowers, although of the same form, are distinguishable by a pale pink instead of a porcelain pink coloring, said pale pink being less accentuated on the outer surface than on the inner surface, where, in fact, it only appears on the exterior periphery on a whitish background starting from the center.

The variety of rose plant, object of the present invention, is the result of a selective study made on numerous plants formed by grafting the new matter (new eye-bud) issued from a bud mutation of the said variety Sweet Promise.

In view of the interest that would be brought about by the disclosure of the different technical effect presented by the new variety as compared with the original variety, it was advisable to propagate the said new variety on a large scale in order to check its behavior, from the physical as well as the biological point of view.

The results were conclusive and underlined the importance of the disclosure of such a variety, with a view to its industrial exploitation by the professional nurserymen and the producers of cut flowers.

The characters and properties of this new variety, obtained as indicated above, are strictly transmissible by agamic means, also called "asexual," i.e., by any means of vegetative propagation, in particular by grafting an "eye" which will be called in the trade by the name of Pitica 0888 F, and which will be found on industrial plants as well as on cut stems delivered subsequently in the trade.

BRIEF DESCRIPTION OF DRAWINGS

The accompanying drawings show as nearly true as it is reasonably possible, to make the same in a color illustration of this character, typical specimen of the flowers and foliage, illustrated in.

DETAILED DESCRIPTION OF DISCLOSURE

Figures 1, 2, 3, 4, 5, 6, 7, 8, 9, 10, 11, 12, 13, 14, 15, 16:
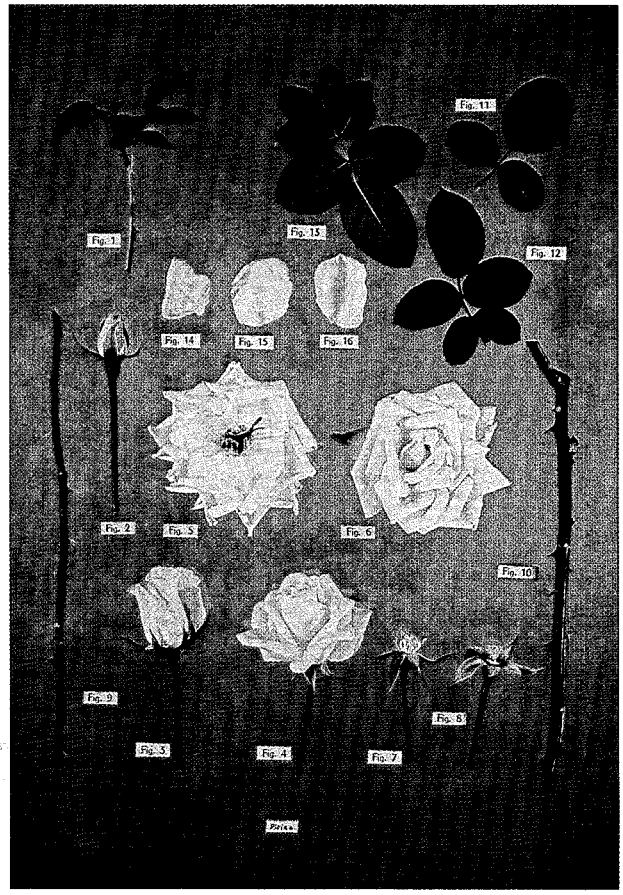
FIG. 1 — a specimen of a young shoot.
FIG. 2 — a specimen of a bud when sepals open.
FIG. 3 — a specimen of a bud when petals open.
FIG. 4 — a specimen of a flower, half-open.
FIG. 5 — a specimen of a flower, fully open, under surface.
FIG. 6 — a specimen of a flower, fully open, upper surface.
FIG. 7 — a specimen of a receptacle, showing, at the time the anthers open, the disposition of the stamens.
FIG. 8 — a specimen of a receptacle showing, at the time the anthers open, the disposition of the pistils (stamens removed)
FIG. 9 — a portion of a flower-bearing stem.
FIG. 10 — a portion of a main branch.
FIG. 11 — a specimen of a leaf with 3 leaflets, upper surface.
FIG. 12 — a specimen of a leaf with 5 leaflets, upper surface.
FIG. 13 — a specimen of a leaf with 7 leaflets, under surface.
FIG. 14 — a specimen of petal, under surface, when the first petal opens.
FIG. 15 — a specimen of a petal under surface, when the flower is half-open.
FIG. 16 — a specimen of petal, upper surface, when the flower is half-open.

Made from a plant growing under glass

Thus will be obtained once again the rose variety — object of the patent — whose botanical and descriptive characteristics as observed on plants grown under glass, at Antibes, Alpes-Maritimes, France, are listed below:

(The Chart used for identification of the colors is that of the Royal Horticultural Society (R.H.S. Color Chart). The terminology preceding the numbered references, proper to this Chart, has been added to designate, in common terms, the corresponding colors).

Class: Grandiflora.

Plant:

*Height.*—On plants cut down to Om. 85, the length of the flowering stems for cutting is the same as that of Sweet Promise — between 50 and 70 cms.

*Habit.*—Straight.

Branches:

*Color.*—Young stems: lettuce green 144/B (yellow-green group). Mature wood: medium green (green group).

*Prickles.*—Shape: upper edge — straight; under edge — concave; base — oval. Size: medium.

Quantity: average, with rare intermixed needle-shaped points. Color: on young stems — reddish; on mature wood — light green, then straw and havana brown.

Leaves:

*Stipules.*—Adnate, pectinate, narrow.

*Petioles.*—Obverse: light green. Reverse: light green.

*Leaflets.*—Number: 3, 5, 7, rarely 9. Shape: rounded. Teeth: single and fairly even. Texture: leathery. General effect: foliage fairly ample and dense, shiny. Color: Young foliage — upper surface: medium green 137/C (green group); under surface: light green 138/B (green group); Adult foliage — upper surface: dark green 147/A (yellow green group); under surface: light green 191/B (greyed green group).

Inflorescence:

*Number of flowers.*—One per stem.

*Peduncle.*—Straight, rigid and thorny.

*Sepals.*—Normal, slightly appendiculate; hairy and whitish inside, smooth and light green outside.

*Bud.*—Shape: elongated. Length: 2, 8 cms. outside of the calyx, when sepals start to open. Size: medium. Color: when opening. — inside: pale pink 37/B (red group) pale yellow unguis 4/C (yellow group); outside: pale pink 37/C (red group) pale yellow 4/C unguis (yellow group).

*Flower.*—Form: high-centered, overlapping petals, with lateral reflexed edges. Double flower — Diameter; 10/11 cms. when fully open. Color: at the opening — inside: pale pink 36/A (red group) touched up, more or less, with 36/D (red group) pale yellow unguis; outside: pale pink 36/C (red group) touched up with 36/D (red group) whitish unguis. While opening — inside: pale pink 36/C (red group) touched up more or less with 36/A — yellowish unguis; outside: very pale pink 36/D (red group) whitish unguis. When fully open — inside: pale pink 36/C (red group) whitish unguis; outside: pale pink 36/D (red group) on the outer periphery, then white towards the center. Fragrance: light. Lasting quality: good, when cut. Corolla: petals — texture: very firm; shape: widely rounded at tip — base more or less wedge-shaped. reflexed lateral edges; number: 25–30. The petals fall off cleanly. stamens: number — 120 on an average; anthers — normal, light yellow; filaments — straight, fairly long and yellow. pistils: number — 70 on an average; stigmas — normal, yellowish; styles — of the same length as the filaments of the stamens. They are whitish yellow at the base and slightly fuchsine at the tips. More or less twisted when coming out of the receptacle. receptacle: smooth, light green; it is narrow and in the shape of a pitcher when cut lengthwise.

Development:

*Vegetation.*—vigorous.

*Flowering.*—Continuous under glass.

*Resistance to diseases.*—Good resistance.

I claim:

1. A new and distinct variety of Grandiflora rose plant, of vegetative reproduction, characterized by the fact that:

from the physical point of view, the plant, with medium green adult wood, is erect, the flower is double, pale pink, its petals are very firm and overlapping;

from the biological point of view, this rose plant is of vigorous vegetation, its re-blooming capacity is excellent, its flowers last a long time either on the plant or when cut;

substantially as shown and described.

* * * * *